United States Patent
Bache

(10) Patent No.: US 10,092,424 B2
(45) Date of Patent: *Oct. 9, 2018

(54) ADJUSTABLE SOCKET SYSTEM

(71) Applicant: OSSUR HF, Reykjavik (IS)

(72) Inventor: Andrew Bache, Reykjavik (IS)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,987

(22) Filed: May 29, 2015

(65) Prior Publication Data
US 2015/0257905 A1    Sep. 17, 2015

Related U.S. Application Data

(63) Continuation of application No. 14/445,248, filed on Jul. 29, 2014, now Pat. No. 9,248,033, which is a
(Continued)

(51) Int. Cl.
*A61F 2/80* (2006.01)
*A61F 2/78* (2006.01)
(Continued)

(52) U.S. Cl.
CPC .................. *A61F 2/80* (2013.01); *A61F 2/66* (2013.01); *A61F 2/78* (2013.01);
(Continued)

(58) Field of Classification Search
CPC ..................................... A61F 2/78; A61F 2/80
See application file for complete search history.

(56) References Cited

U.S. PATENT DOCUMENTS

| 37,282 A | 1/1863 | Engelbrecht et al. |
| 51,593 A | 12/1865 | Jewett |

(Continued)

FOREIGN PATENT DOCUMENTS

| DE | 319623 C | 3/1920 |
| EP | 1433447 A2 | 6/2004 |

(Continued)

OTHER PUBLICATIONS

Lynde, 1918, 127,451, Improvements in Artificial Limbs an the Like.*

(Continued)

*Primary Examiner* — Bruce E Snow
(74) *Attorney, Agent, or Firm* — Workman Nydegger

(57) ABSTRACT

An adjustable prosthetic socket includes proximal and distal ends and an axis extending between the proximal and distal ends. A distal base is adapted to support a distal portion of a residual limb and is located at the distal end of the socket. At least one spine extends upwardly from the distal base toward the proximal end. The at least one spine defines at least part of a circumference of the socket about the axis. A proximal support is located at or near the proximal end of the socket and extends from the at least one spine. The proximal support is arranged to distribute pressure from the at least one spine over a portion of the residual limb. A tensioning system is operatively connected to the at least one spine and arranged to selectively adjust the circumference of the socket.

14 Claims, 12 Drawing Sheets

Related U.S. Application Data continuation of application No. 13/277,590, filed on Oct. 20, 2011, now Pat. No. 8,795,385.

(60) Provisional application No. 61/405,766, filed on Oct. 22, 2010.

(51) Int. Cl.
   *A61F 2/66* (2006.01)
   *A61F 2/50* (2006.01)

(52) U.S. Cl.
   CPC ............ *A61F 2002/5027* (2013.01); *A61F 2002/6614* (2013.01); *A61F 2002/7862* (2013.01); *A61F 2002/7881* (2013.01); *A61F 2220/0025* (2013.01)

(56) References Cited

U.S. PATENT DOCUMENTS

| | | | |
|---|---|---|---|
| 366,494 A | 7/1887 | Marks | |
| 470,431 A | 3/1892 | Marks | |
| 1,066,605 A | 7/1913 | Hanger | |
| 1,082,256 A * | 12/1913 | Apgar | A61F 2/601 623/31 |
| 1,144,681 A * | 6/1915 | Apgar | A61F 2/601 623/33 |
| 1,861,311 A | 5/1932 | Logan | |
| 1,893,853 A | 1/1933 | Tullis | |
| 2,025,835 A | 12/1935 | Trautman | |
| 2,229,728 A | 1/1941 | Eddels | |
| 2,634,424 A | 4/1953 | O'Gorman | |
| 2,669,728 A | 2/1954 | Ritchie | |
| 4,128,903 A | 12/1978 | Marsh et al. | |
| 4,161,042 A * | 7/1979 | Cottingham | A61F 2/60 623/33 |
| 4,268,922 A | 5/1981 | Marsh et al. | |
| 4,283,800 A | 8/1981 | Wilson | |
| 4,300,245 A | 11/1981 | Saunders | |
| 4,459,709 A | 7/1984 | Leal et al. | |
| 4,783,293 A | 11/1988 | Wellershaus et al. | |
| 4,842,608 A | 6/1989 | Marx et al. | |
| 4,872,879 A | 10/1989 | Shamp | |
| 4,921,502 A | 5/1990 | Shamp | |
| 4,938,775 A | 7/1990 | Morgan | |
| 4,988,360 A | 1/1991 | Shamp | |
| 5,108,456 A | 4/1992 | Coonan, III | |
| 5,133,777 A | 7/1992 | Arbogast et al. | |
| 5,201,773 A | 4/1993 | Carideo, Jr. | |
| 5,201,775 A | 4/1993 | Arbogast et al. | |
| 5,246,464 A | 9/1993 | Sabolich | |
| 5,312,669 A | 5/1994 | Bedard | |
| 5,424,782 A | 6/1995 | Aoki | |
| 5,503,543 A | 4/1996 | Laghi | |
| 5,529,575 A | 6/1996 | Klotz | |
| 5,545,231 A | 8/1996 | Houser | |
| 5,571,209 A | 11/1996 | Brown, Sr. | |
| 5,651,792 A | 7/1997 | Telikicherla | |
| 5,653,766 A | 8/1997 | Naser | |
| 5,718,925 A | 2/1998 | Kristinsson et al. | |
| 5,724,714 A | 3/1998 | Love | |
| 5,728,165 A | 3/1998 | Brown, Sr. | |
| 5,800,565 A | 9/1998 | Biedermann | |
| 5,824,111 A | 10/1998 | Schall et al. | |
| 5,885,509 A | 3/1999 | Kristinsson | |
| 5,888,215 A | 3/1999 | Roos et al. | |
| 5,888,217 A | 3/1999 | Slemker | |
| 5,897,517 A | 4/1999 | Laghi | |
| 6,033,440 A | 3/2000 | Schall et al. | |
| 6,051,026 A | 4/2000 | Biedermann et al. | |
| 6,228,124 B1 | 5/2001 | Slemker et al. | |
| 6,231,618 B1 | 5/2001 | Schall et al. | |
| 6,368,357 B1 | 4/2002 | Schon et al. | |
| 6,406,499 B1 | 6/2002 | Kania | |
| 6,458,163 B1 | 10/2002 | Slemker et al. | |
| 6,497,028 B1 | 12/2002 | Rothschild et al. | |
| 6,500,210 B1 | 12/2002 | Sabolich et al. | |
| 6,557,177 B2 | 5/2003 | Hochmuth | |
| 6,793,682 B1 | 9/2004 | Mantelmacher | |
| 6,942,703 B2 | 9/2005 | Carstens | |
| 6,991,657 B1 | 1/2006 | Price, Jr. | |
| 7,090,700 B2 | 8/2006 | Curtis | |
| 7,094,212 B2 | 8/2006 | Karason et al. | |
| 7,097,799 B1 | 8/2006 | Burton | |
| 7,105,122 B2 | 9/2006 | Karason | |
| 7,118,602 B2 | 10/2006 | Bjarnason | |
| 7,172,714 B2 | 2/2007 | Jacobson | |
| 7,240,414 B2 | 7/2007 | Taylor, Sr. | |
| 7,288,116 B2 | 10/2007 | Ikeda | |
| 7,338,532 B2 | 3/2008 | Haberman et al. | |
| 7,344,567 B2 | 3/2008 | Slemker | |
| 7,402,265 B2 | 7/2008 | Jacobson | |
| 7,488,349 B2 | 2/2009 | Einarsson | |
| 7,727,284 B2 | 6/2010 | Warila | |
| 7,867,286 B2 | 1/2011 | Einarsson | |
| 7,985,192 B2 | 7/2011 | Sheehan et al. | |
| 8,007,544 B2 | 8/2011 | Jonsson et al. | |
| 8,083,807 B2 | 12/2011 | Auberger et al. | |
| 8,088,320 B1 | 1/2012 | Bedard | |
| 8,123,818 B2 | 2/2012 | Bjarnason et al. | |
| 8,303,527 B2 | 11/2012 | Joseph | |
| 8,308,815 B2 | 11/2012 | McCarthy | |
| 8,323,353 B1 | 12/2012 | Alley et al. | |
| 8,414,658 B2 | 4/2013 | Johnson et al. | |
| 8,470,050 B2 | 6/2013 | Dillingham | |
| 8,480,758 B2 | 7/2013 | McLeod | |
| 8,491,667 B2 | 7/2013 | Dillingham | |
| 8,795,385 B2 | 8/2014 | Bache | |
| 8,845,755 B2 | 9/2014 | Dillingham | |
| 9,050,202 B2 | 6/2015 | Bache et al. | |
| 9,248,033 B2 | 2/2016 | Bache | |
| 9,572,691 B2 | 2/2017 | Pacanowsky et al. | |
| 2002/0099450 A1 | 7/2002 | Dean, Jr. et al. | |
| 2003/0181990 A1 | 9/2003 | Phillips | |
| 2005/0209706 A1 | 9/2005 | Warila | |
| 2005/0278039 A1 | 12/2005 | Nobbe | |
| 2006/0009860 A1 | 1/2006 | Price, Jr. | |
| 2006/0135902 A1 | 6/2006 | Ingimundarson et al. | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2008/0066272 A1 | 3/2008 | Hammerslag et al. | |
| 2008/0269914 A1 | 10/2008 | Coppens et al. | |
| 2009/0076625 A1 | 3/2009 | Groves et al. | |
| 2009/0105844 A1 | 4/2009 | Ortiz | |
| 2009/0287128 A1 * | 11/2009 | Ingimundarson | A61F 5/0111 602/27 |
| 2010/0030344 A1 | 2/2010 | Hansen et al. | |
| 2010/0036300 A1 | 2/2010 | Sheehan et al. | |
| 2010/0036505 A1 | 2/2010 | Hassler | |
| 2010/0082116 A1 * | 4/2010 | Johnson | A61F 2/54 623/59 |
| 2010/0121464 A1 | 5/2010 | Mantelmacher | |
| 2010/0191348 A1 | 7/2010 | Kettwig et al. | |
| 2010/0274364 A1 | 10/2010 | Pacanowsky et al. | |
| 2011/0035027 A1 | 2/2011 | McCarthy | |
| 2011/0071647 A1 | 3/2011 | Mahon | |
| 2011/0114635 A1 | 5/2011 | Sheehan | |
| 2011/0232837 A9 | 9/2011 | Ottleben | |
| 2011/0320010 A1 | 12/2011 | Vo | |
| 2012/0022667 A1 | 1/2012 | Accinni et al. | |
| 2012/0041567 A1 | 2/2012 | Cornell | |
| 2012/0095570 A1 | 4/2012 | Marquette | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0253475 A1 | 10/2012 | Kelley et al. | |
| 2012/0259432 A1 | 10/2012 | Dillingham | |
| 2012/0271210 A1 | 10/2012 | Galea et al. | |
| 2012/0271433 A1 | 10/2012 | Galea et al. | |
| 2012/0283846 A1 | 11/2012 | Janssen et al. | |
| 2013/0123940 A1 | 5/2013 | Hurley et al. | |
| 2013/0245785 A1 | 9/2013 | Accini et al. | |
| 2015/0018974 A1 | 1/2015 | Dillingham | |

(56) References Cited

U.S. PATENT DOCUMENTS

| | | | |
|---|---|---|---|
| 2015/0230945 | A1 | 8/2015 | Bache et al. |
| 2016/0278949 | A1 | 9/2016 | Dillingham |
| 2016/0331562 | A1 | 11/2016 | Bache et al. |

FOREIGN PATENT DOCUMENTS

| | | | |
|---|---|---|---|
| EP | 1656911 A1 | 5/2006 |
| GB | 127 451 A | 6/1919 |
| GB | 675811 A | 7/1952 |
| GB | 2169207 A | 7/1986 |
| RU | 2088182 C1 | 8/1997 |
| WO | 91/16019 A1 | 10/1991 |
| WO | 98/12994 A1 | 4/1998 |
| WO | 2007/035875 A2 | 3/2007 |
| WO | 2008/116025 A2 | 9/2008 |
| WO | 2009/093020 A2 | 7/2009 |
| WO | 2012/021823 A1 | 2/2012 |
| WO | 2013/071308 A1 | 5/2013 |

OTHER PUBLICATIONS

International Search Report and Written Opinion Issued of PCT/US2011/057043, dated Jan. 27, 2012, 10 pages.
Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.
International Search Report from Corresponding PCT Application No. PCT/US2013/048675, dated Oct. 9, 2013.
Manual: "Socket Evaluation System with the Rapid Adjustment Pylon", [retrieved from the internet on May 22, 2014], 4 pages. <URL:http://www.fillauer.com>; 4 pages.
Fairley, M. "M.A.S. Socket: A Transfemoral Revolution", The O&P Edge, Jun. 2004, www.oandp.com/articles/2004-06_03.asp. 5 Pages.
Gard, S.A. "Overview of Lower Limb Prosthetics Research", WRAMC and the VA Orthopedic & Prosthetic Workshop Arlington, VA, Nov. 17-18, 2003, pp. 1-49.
Greenwald, et al., "Volume Management: Smart Variable Geometry Socket (SVGS) Technology for Lower-Limb Prostheses", American Academy of Orthotists & Prosthetists, vol. 15, No. 3, 2003, pp. 107-112.
Koike, et al., "The TC Double Socket Above-knee Prosthesis", Prosthetics and Orthotics International, vol. 5, 1981 pp. 129-134.
Krouskop, et al., "Computer-aided design of a prosthetic socket for an above-knee amputee", Journal of Rehabilitation Research and Development, vol. 24, No. 2 1987, pp. 31-38.
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 27, No. 1; pp. 71-74.
Smith, "Silver Linings for O&P Devices", The Academy Today, vol. 1, No. 4: Oct. 2005, 4 Pages, Downloaded from, http://www.oandp.org/AcademyTODAY/20050ct/7.asp.
Spaeth, JP, "Laser Imaging and Computer-Aided Design and Computer-Aided Manufacture in Prosthetics and Orthotics", Physical Medicine and Rehabilitation Clinics of North America, Elsevier Publishing, Amsterdam, The Netherlands; Feb. 2006 pp. 245-263, Abstract. 2 pages.
Wilson, "Recent Advances in Above-Knee Prosthetics", Artificial Limbs, vol. 12, No. 2, 1968 pp. 1-27.
Wu, et al, "CIR sand casting system for trans-tibial socket", Prosthetics and Orthotics International, Aug. 2003: vol. 27, pp. 146-152.
Extended Search Report from European Patent Application No. 12847452.5, dated Jul. 21, 2015.
International Search Report for International Application No. PCT/US2012/064876, dated Feb. 19, 2013.
Written Opinion of the International Searching Authority for International Application No. PCT/US2012/064876, dated Feb. 19, 2013.
International Search Report for International Application No. PCT/US2014/029773, dated Jun. 13, 2014.
International Search Report from PCT Application No. PCT/2016/031615, dated Jul. 12, 2016.
Written Opinion of the International Searching Authority for International Application No. PCT/US2014/043500, dated Aug. 14, 2014.
International Search Report for International Application No. PCT/US2014/043500, dated Aug. 18, 2014.
International Search Report for International Application No. PCT/US15/021611, dated Jun. 25, 2015.
Written Opinion of the International Searching Authority for International Application No. PCT/US15/021611, dated Jun. 25, 2015.
International Search Report for International Application No. PCT/US2014/070666, dated Mar. 31, 2015.
Written Opinion of the International Searching Authority for International Application No. PCT/US2014/070666, dated Mar. 31, 2015.
Quigley, Michael, "Prosthetic Management: Overview, Methods and Materials," Chapter 4, Atlas of Limb Prosthetics: Surgical, Prosthetic, and Rehabilitation Principles, Second Edition, 1992, 10 Pages. Downloaded from: http://www.bandplibrary.org/alp/chapot-01.asp.
Burgess, et al. "Immediate Post-Surgical Prosthetic Fitting", The Management of Lower-Extremity Amputations, Aug. 1969, pp. 42-51.
Compton, et al., "New Plastics for Forming Directly on the Patient", Prosthetics and Orthotics International, 1978, vol. 2, No. 1, pp. 43-47, Abstract. 3 Pages.
Fairley, "Socket Can Be Fabricated, Modified, Fitted—In One Hour", The O&P EDGE, Jun. 2007. 5 Pages.
"Cut-4-Custom: Custom TLSO in Less Than an Hour", The O&P EDGE, Oct. 2010. 2 Pages.
Written Opinion of the International Searching Authority for International Application No. PCT/US2014/029773, dated Jun. 13, 2014.
International Search Report from PCT Application No. PCT/US2018/016802, dated May 2, 2018.

* cited by examiner

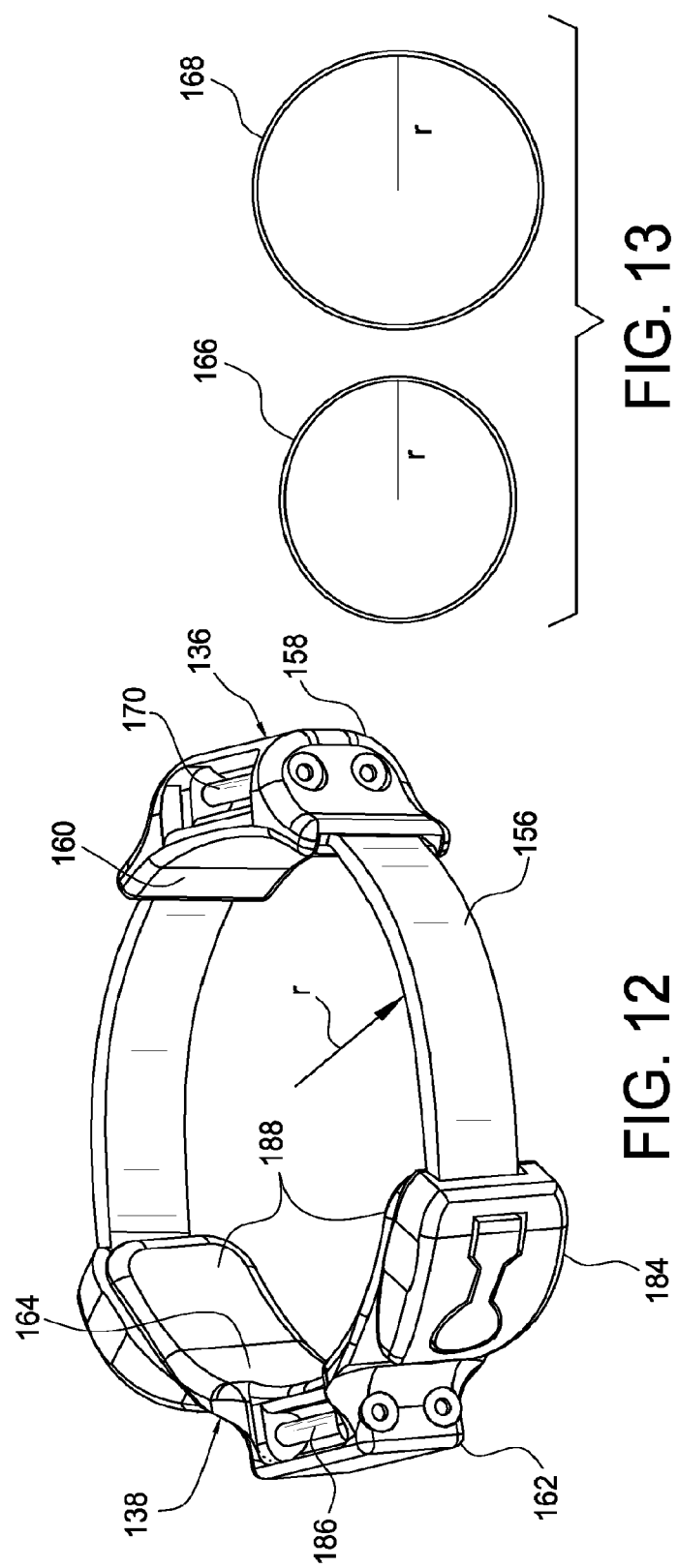

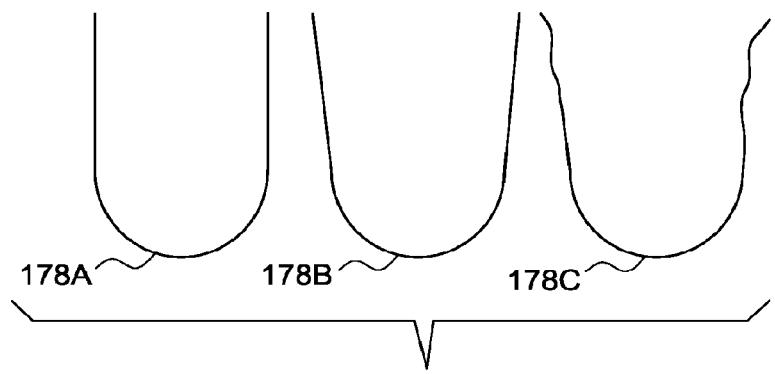
FIG. 16
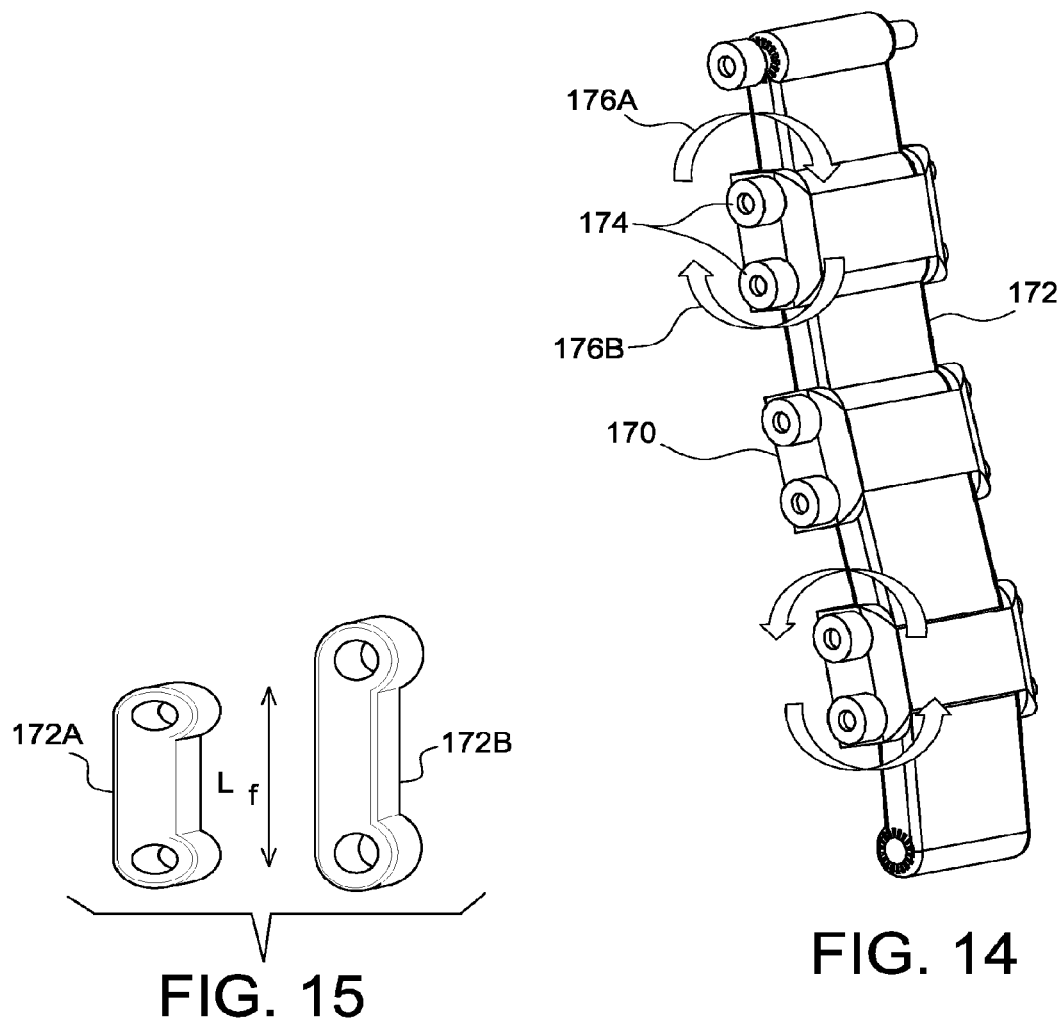
FIG. 15
FIG. 14

ADJUSTABLE SOCKET SYSTEM

CROSS-REFERENCE TO RELATED APPLICATION

This application is continuation of U.S. application Ser. No. 14/445,248, filed Jul. 29, 2014, which is a continuation of U.S. application Ser. No. 13/277,590, filed Oct. 20, 2011, now U.S. Pat. No. 8,795,385 which claims priority to U.S. Provisional Patent Application 61/405,766, filed Oct. 22, 2010, each of which is incorporated herein by reference.

FIELD OF THE INVENTION

The invention relates to the field of prosthetic devices, and more particularly to an adjustable socket for accommodating a residual limb.

BACKGROUND

A socket is commonly referred to as the portion of a prosthesis that fits around and envelopes a residual limb or stump, and to which prosthetic components, such as a foot, are attached. When providing a socket to an amputee, it is essential to properly fit the socket and align various parts of the prosthesis to the amputee. Fitting and alignment of the socket are difficult tasks to perform, and require extensive knowledge, training and skill on behalf of the prosthetist.

Typically, sockets for definitive prostheses are customized for a residual limb of a particular wearer. According to one method, the sockets are formed over a model of the stump, such as one formed by plaster-of-paris, in a manner that is used to distribute forces between the socket and the stump in a comfortable way to the amputee. In another method, the socket may be obtained from computer aided design by modeling the shape of the stump, and subsequently forming a model. Once the model is obtained in either of these methods, a socket is formed over the model by using fabric and liquid plastic resin to obtain a definitive rigid socket customized to a particular limb.

Proper fitting of a socket to the stump is critical to the success of the prosthesis. The socket must fit closely to the stump to provide a firm connection and support, but must also be sufficiently loose to allow for circulation. In combination with proper fitting, the socket must transfer loads from the residual limb to the ground in a comfortable manner.

Most prosthetic sockets are permanently formed to a customized shape that is static, meaning that the socket does not account for shape and volume fluctuations of the residual limb. When there are shape and volume fluctuations, the fitting of the socket is impeded, with these sockets causing discomfort, pain and soft tissue breakdown of the stump. In addition, conventional sockets tend to be bulky and cumbersome to wear, and may be difficult to don making the residual limb uncomfortable when worn.

It is desirable to provide a simplified and compact prosthesis system that overcomes the drawbacks over known prosthesis systems. Particularly, it is advantageous to provide a socket system that is off-the-shelf and capable of accommodating a variety of residual limb sizes. It is also desired that a socket system be adjustable to allow for volume and shape fluctuations, and in effect, provide a dynamic socket as opposed to the known static sockets. The adjustable socket can better adjust for pressure distribution, and maintain comfort to the amputee over a range of care and residual limb conditions.

SUMMARY

The challenges of known socket systems are addressed in accordance with embodiments of the invention providing an adjustable socket system. The adjustable socket system is adapted to receive and fit a range of heights and lengths of a residual limb, as well as accommodate volume and shape fluctuations of a residual limb. From its versatility in fitting and adjustment, the adjustable socket system can decrease pain, discomfort and soft tissue breakdown over known sockets that are static in size and shape. Moreover, the adjustability of the socket provides an off-the-shelf socket system that takes much of the guesswork out of making a socket and provides an instant solution when urgency may be required to provide an amputee with a socket.

In accordance with an embodiment of the invention, an adjustable socket system having first and second opposed sides includes a rigid first component having proximal and distal end areas. The first component is arranged along the first side of the socket. The adjustable socket system further includes an adjustable second component having proximal and distal end areas. The second component has a second plurality of interconnected vertebrae elements connected to the first component, and is arranged along the second side of the socket system. The adjustable socket system includes a base connector secured to the distal end area of the first component. The base connector may also be secured to the distal end area of the second component.

A plurality of flexible and adjustable straps may connect the second plurality of vertebrae to the first component. The first component may also include a first plurality of vertebrae with the first plurality of vertebrae corresponding at least in part to the second plurality of vertebrae. At least some of the first plurality of vertebrae may have parallel or angled mating surfaces.

The individual vertebra of the second plurality of vertebrae may be pivotable relative to one another, and the second component may include a flexible spine upon which the second plurality of vertebrae is secured. Alternatively, the individual vertebra of the second plurality of vertebrae may be pivotable and lockable in position relative to one another. The second component may be flexible relative to the first component which is rigid or semi-rigid.

The adjustable socket system may further include a proximal support having first and second wings for providing medial-lateral support and is secured to the proximal end area of the first component.

The first plurality of vertebrae may have a first plurality of lateral tabs extending from the vertebrae. The second plurality of vertebrae may also have a second plurality of lateral tabs extending from the vertebrae. The lateral tabs may be flexible.

The first and second sides of the adjustable socket may respectively correspond to posterior and anterior aspects of a residual limb.

In accordance with another embodiment of the invention, an adjustable prosthetic socket having first and second opposed sides includes a rigid first component having proximal and distal end areas. The first component has a first plurality of interconnected vertebrae elements and is arranged along the first side of the socket. The socket system further includes an adjustable second component having proximal and distal end areas. The second component has a second plurality of interconnected vertebrae elements connected to the first component and is arranged along the second side of the socket.

The socket further includes at least one tensioning element connecting the first plurality of vertebrae and the second plurality of vertebrae. The at least one tensioning element is connected to at least one tensioner which is configured to adjust the tension of the at least one tensioning element. The socket may also include a base connector secured to the distal end area of the first component and the second component having an adjustable width.

The individual vertebra of the second plurality of vertebrae may be pivotable relative to one another, and the first plurality of vertebrae and the second plurality of vertebrae may have a plurality of lateral tabs extending from the vertebrae.

The numerous advantages, features and functions of the various embodiments of the adjustable socket system will become readily apparent and better understood in view of the following description and accompanying drawings. The following description is not intended to limit the scope of the adjustable socket system, but instead merely provides exemplary embodiments for ease of understanding.

BRIEF DESCRIPTION OF THE DRAWINGS

The inventive orthopedic device is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

FIG. 12 is a perspective view of a circumferential vertebrae assembly of the socket system of FIG. 9.

FIG. 13 is a perspective view of circumferential sizes of the circumferential vertebrae assembly of FIG. 12 for a residual limb.

FIG. 14 is a perspective view of an elongate vertebrae assembly of the socket system of FIG. 9.

FIG. 15 shows a plurality of differently sized vertebra struts.

FIG. 16 shows a plurality of differently sized residual limb profiles.

DETAILED DESCRIPTION OF VARIOUS EMBODIMENTS

A. Overview

Figure 1:
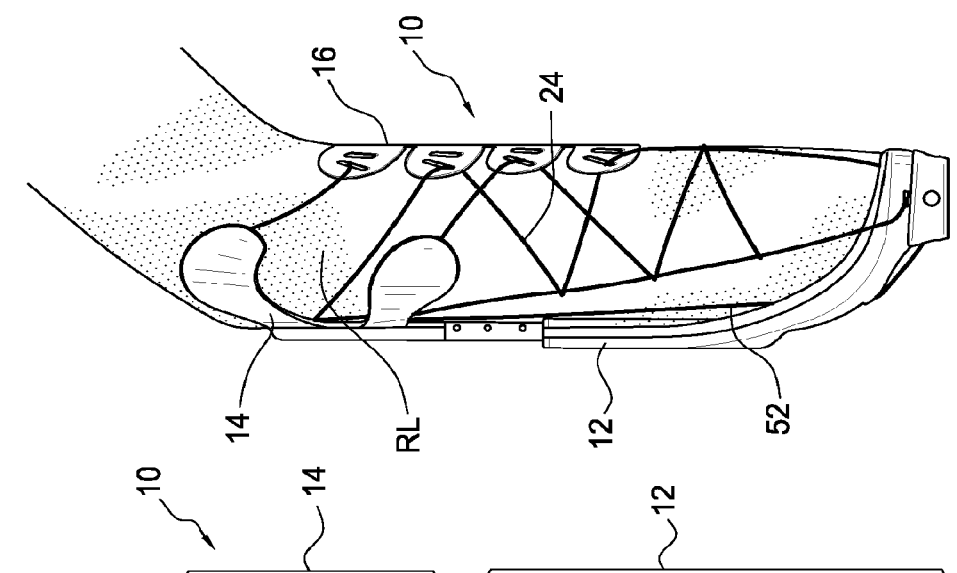
FIG. 1 is an elevational side view showing an embodiment of the adjustable socket system.
Figure 2:
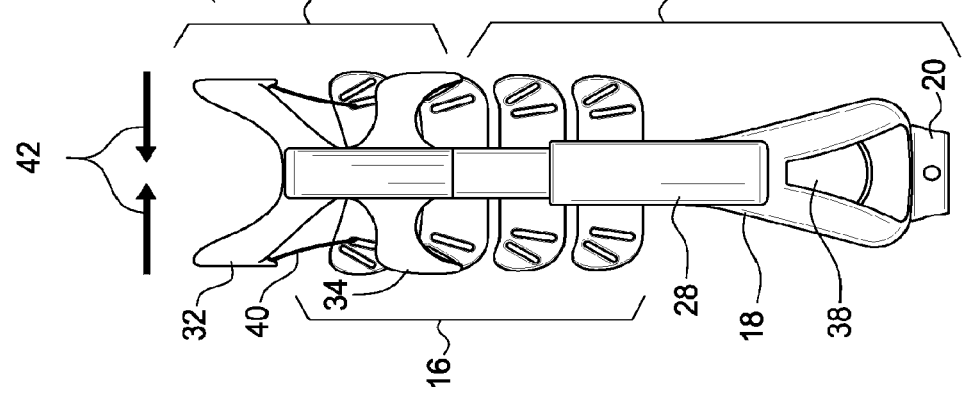
FIG. 2 is an elevational view showing the anterior side of the socket system according to FIG. 1.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "mean" or "step" clause as specified in 35 U.S.C. § 112, paragraph 6.

The anatomical terms described herein are not intended to detract from the normal understanding of such terms as readily understood by one of ordinary skill in the art of prosthetics. For example, the term "distal" is used to denote the portion or end of a limb that is farthest from the central portion of the body. The term distal is the opposite of "proximal" which is used to denote that the end or portion of the limb is nearer to the central portion of the body.

Some of the components described herein share similarities to components in U.S. Pat. No. 7,488,349 and pending U.S. application Ser. No. 12/275,459.

B. Embodiments of the Adjustable Socket System

In accordance with an embodiment of the invention, FIG. 1 illustrates an adjustable socket system 10 that is adapted to receive and fit a range of heights and lengths of a residual limb, as well as accommodate volume and shape fluctuations of a residual limb. From its versatility in fitting and adjustment, the adjustable socket system can decrease pain, discomfort and soft tissue breakdown over known sockets that are static in size and shape. Moreover, the adjustability of the socket provides an off-the-shelf socket system that takes much of the guesswork out of making a socket and provides an instant solution when urgency may be required to provide an amputee with a socket.

The adjustable socket system 10 depicted in FIGS. 1-8 is configured to receive a residual limb from a transtibial level amputation. It will be understood, however, that the adjustable socket system may be adapted to receive a variety of different types of amputations, whether configured for the leg or arm.

Turning to the details of the embodiment of the socket system 10, the socket system is shown as having a rigid strut device 12, a semi-flexible anterior clamp element 14 adjustably secured to the rigid strut device 12, a semi-flexible posterior clamp element 16, and a strap system 24 connecting the strut device 14, the anterior clamp element 14 and the posterior clamp element 16.

The strut device 12 is sufficiently rigid to resist deflection or bending, and stably holds the residual limb when it transfers weight bearing forces from the residual limb to the ground. The strap system 24 functions as a weight bearing, flexible bag that contains the residual limb and maintains it in connection to the strut device 12. The clamp elements 14, 16, in combination with the strut device and the strap system, serve to clamp firmly the proximal portion of the residual limb, and distribute pressure exerted on the limb by the strap system.

Figure 3:
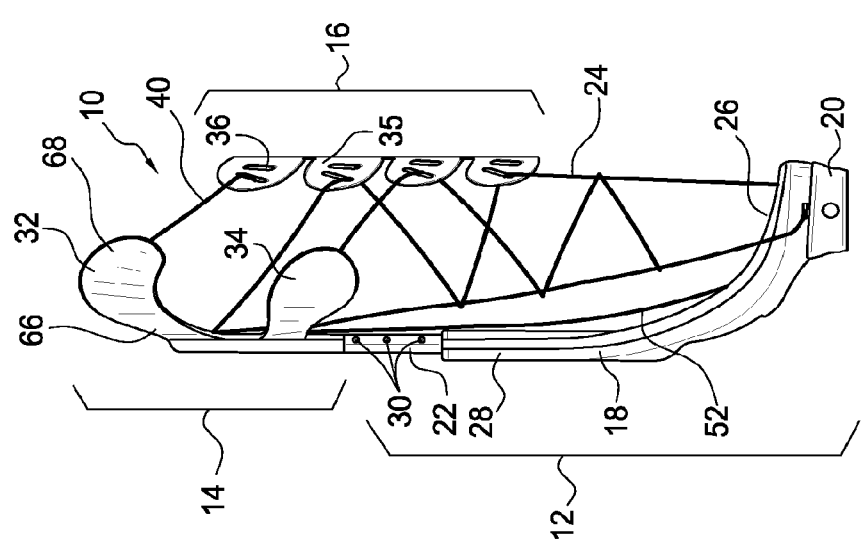
FIG. 3 is an elevational view of the socket system of FIG. 1 showing a "bow" strap.
Figure 4:
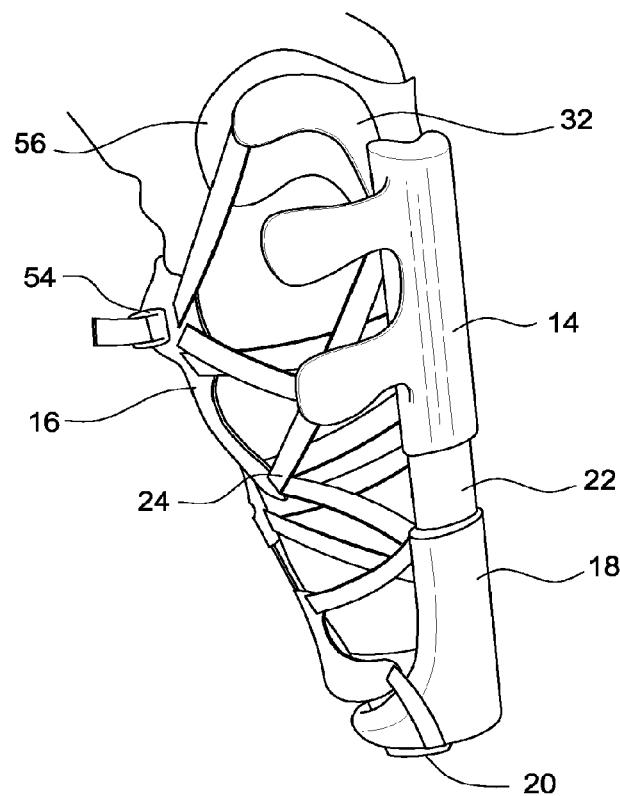
FIG. 4 is a schematic view of the socket system according to FIG. 1 shown on a residual limb.
Figure 5:
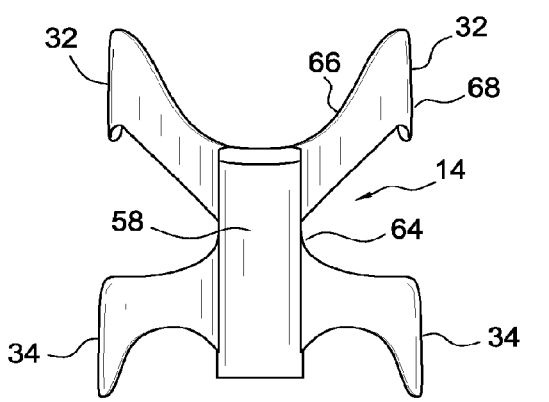
FIG. 5 is an anterior view of the anterior clamp element according to the socket system of FIG. 1.
Figure 6:
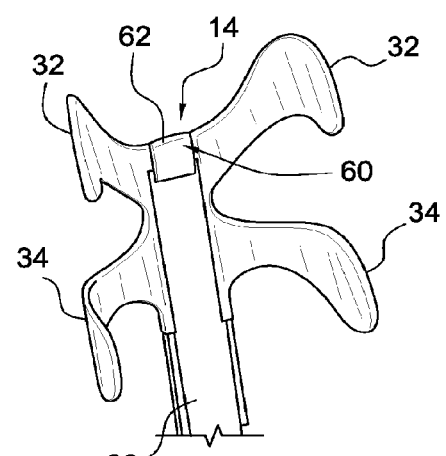
FIG. 6 is a perspective view of the anterior clamp element mounted on a strut according to the socket system of FIG. 1.
Figure 7:
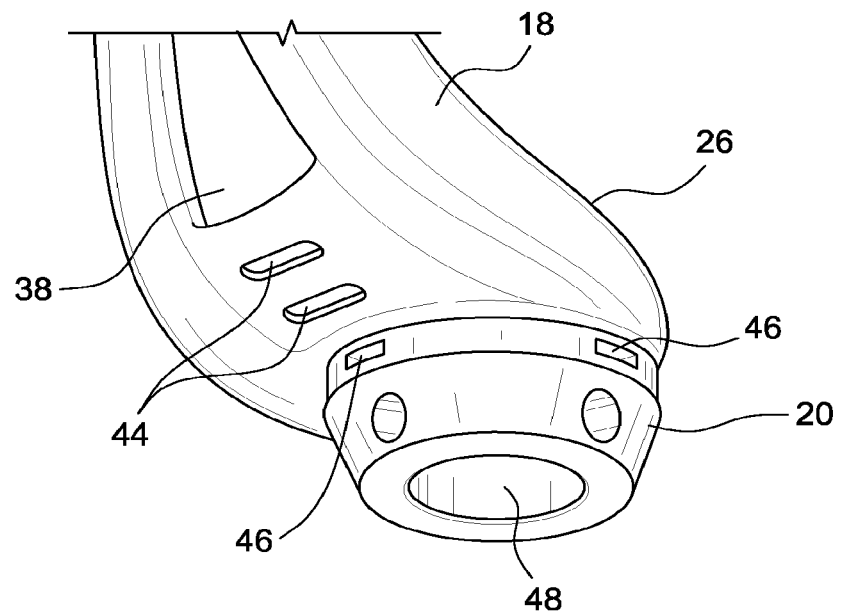
FIG. 7 is a perspective view of an underside of the distal end of the strut base according to the socket system of FIG. 1.
Figure 8:
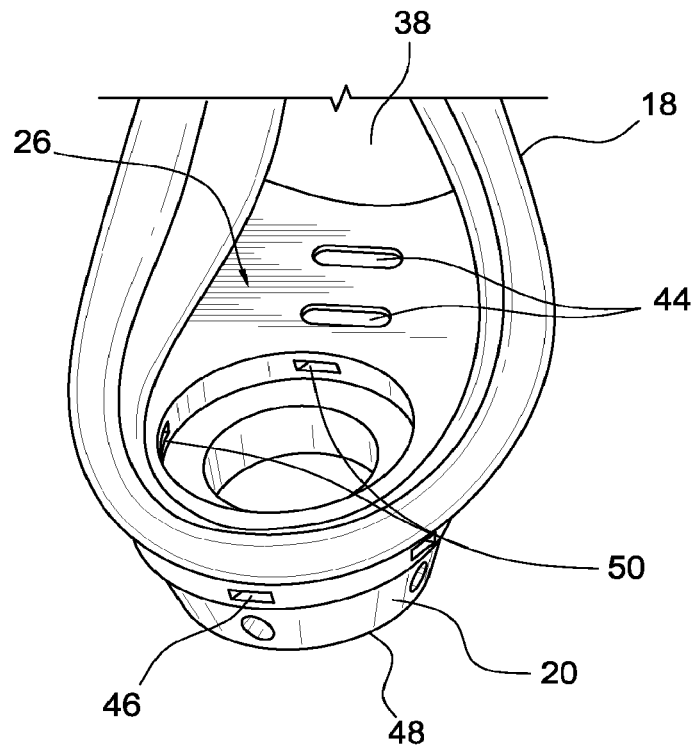
FIG. 8 is a perspective view of topside of the distal end of the strut base according to the socket system of FIG. 1.

As depicted in FIGS. 3 and 4, the socket system 10 is configured to be worn on the residual limb RL of a transtibial amputee. The strut device 12 is mounted along the anterior side of the residual limb, and along the saggital plane of the leg. The strut device receives the distal end portion of the residual limb, and the anterior and posterior clamp elements embrace the proximal portion of the residual limb, on anterior and posterior sides, respectively, of the residual limb RL. Specifically, in this embodiment, the anterior and posterior clamp elements generally correspond to the condylar regions of the residual limb RL.

The strap system 24 runs along at least the anterior side of the residual limb, such as with a bow strap 52 discussed more fully below, and along medial and lateral portions of the residual limb so as to form a bag about the leg. From this system of connections, the socket system secures the anterior, posterior, lateral and medial sides of the residual limb.

1. First Embodiment of the Socket System a. Strut Device

The strut device is connected to a flexible network of straps forming the strap system, the semi-flexible clamp elements and a prosthetic component system, such as a foot, pylon and other components.

The strut device 12 has a strut base 18 forming a limb receiving portion or seat 26 adapted to receive a distal end portion of a residual limb and an anterior opening 38 arranged for ventilating the rigid strut and accommodating minor fluctuations of the volume of the residual limb.

A base connector 20 is secured to a bottom portion of the strut base 18, and is adapted to connect to prosthetic components, such as an artificial foot, and serve as a connection point for various straps of the strap system. The strut base 18 forms a sleeve 28 at an upper part thereof, and an adjustable strut 22 slidably engages the sleeve 28 and is lockable at a plurality of predefined height settings 30.

The limb seat 26 defines a plurality of slots 44 on the anterior side arranged for receiving straps from the strap system, particularly the bow strap 52. The slots 44 allow for adjustment of the strap for anterior/posterior adjustment, as well as for medial and lateral adjustment.

The limb seat 26 also defines a plurality of fixation openings 46 located on an outer side of the strut device 12, and arranged receive strap end portions. The inner side of the limb seat 26 defines holes 50 adapted to receive a fastener in order to secure the strap ends to the strut device 12 at the distal end.

The base connector may be a coupling 48 in the form of a male/female pyramid adapter allowing the strut device to connect to a variety of commercially available components, as would be understood by the skilled person. In another variation, the base connector itself may be formed as a prosthetic foot, such that the socket system in combination with the foot attached therewith forms a complete off-the-shelf prosthesis.

b. Strap System

The strut device and the clamp elements are linked to one another by the strap system. The strap system comprises a plurality of straps that bear weight of the amputee and embrace the residual limb.

One of the straps forming the strap system is a bow strap 52, as shown in FIGS. 1 and 3. The bow strap 52 is an elongate vertical strap extending between the proximal and distal portions of the socket system. Specifically, the bow strap is mounted to the anterior clamp element 14, particularly at the sleeve 58, and is adjustably secured to the strut base 18 at one of the slots 44. The bow strap 52 extends along the strut device, and according to a variation of the embodiment may extend against the strut device 12 along its length.

The bow strap is flexible so as to accommodate the residual limb yet it is under sufficient tension to provide stability and weight bearing functionality. The bow strap is preferably non-stretchable. Other straps of the strapping system may be attached directly to the bow strap.

The fixation point of the bow strap to the strut base is achieved by passing an end portion of the bow strap through one of the fixation slots 44 arranged in a series of rows extending between the anterior and posterior sides of the socket system. From the arrangement of the rows, the bow strap can be particularly arranged for anterior and posterior adjustment. The fixation slots 44 may also be configured sufficiently wide to allow for medial and lateral adjustment of the bow strap.

As noted, the limb seat 26 defines a plurality of fixation openings 46 for receiving strap ends and holes 50 adapted to receive a fastener in order to secure the strap ends to the strut device 12 at the distal end. By mounting the straps at the distal end of the strut device, the straps can be placed in high tension, and can be adjusted for tension.

A variety of different strap systems may be used herein in combination with the strut device and the clamp elements. In one variation, the strap system comprises a network of interconnected straps that alternately secure to the anterior and posterior clamp elements as well as to the bow strap. These straps may be tensioned by a single strap tensioner or multiple strap tensioners 54. This combination of straps functions similarly to a "Chinese finger trap" in that the network of interconnected straps are tightened with minimal adjustment, or may automatically tighten as an amputee places the residual limb into the socket system.

According to another variation of the strap system, each strap may be adjusted individually by a strap tensioner. This type of strap system comprising individual straps allows for targeted adjustment of the strap system.

In yet another variation, the strap system may include a combination of a network of straps and a plurality of straps that are individually adjusted. For example, the upper strap 40 connecting the anterior clamp element to the posterior clamp element may be individually adjusted, whereas the remainder of the straps may form part of a strap network that is adjusted by a single tensioner.

It will be understood that the strap system may include a combination of stretchable and non-stretchable straps, as prescribed locations to accommodate certain residual limb geometries or loading.

c. Clamp Elements

The anterior clamp element 14 secures to an upper end of the strut 22 via a sleeve 58 formed by the anterior clamp element 14. The sleeve 58 securely receives the strut 22, and forms a substantially rigid portion of the anterior clamp element 14. The anterior clamp element 14 is preferably semi-flexible so that when straps, as in upper strap 40, connected to the anterior clamp element are tensioned, the anterior clamp element 14 can flexibly yield in part to the anatomy of the residual limb while withstanding loads exerted thereon by the amputee. Suitable padding 56 is provided against the anterior clamp element, as would be available to the skilled person.

The semi-flexibility of the anterior clamp element is defined in part as having the property as being partially or somewhat flexible, such that the clamp element can bend about anatomy but still have sufficient rigidity and strength to withstand pressure exerted thereon by loads from the residual limb and weight of the amputee.

The semi-flexibility of the anterior clamp element may be obtained in part by the material used to form the clamp element as well as the geometry of the clamp element. Specifically, the geometry of the anterior clamp element 14 includes upper and lower wings 32, 34 on opposed sides of the clamp element, and extending a distance from the strut 22, and spaced apart in height by a gap 64 formed between the upper and lower wings 32, 34.

Each wing 32, 34 defines an arm 66 flexibly extending from the sleeve 58 and includes a head 68 adapted to grasp part of the residual limb. The head is sufficiently configured to distribute pressure over the residual limb when a strap connected thereto is tensioned. The arm 66 bends relative to the sleeve 58, and may have a thickness less than the thickness of the sleeve 58.

The wings 32, 34 of the anterior clamp element 14 are secured to posterior wings 36 of the posterior clamp element 16 by the strap system. Like the anterior wings 32, 34, the posterior wings 36 flex relative to an elongate base portion 35 of the posterior clamp element. The posterior base portion 35 is more rigid than the posterior wings 36.

The combination of the semi-flexible anterior clamp element and the semi-flexible posterior clamp element with the strap system permits the socket system to adjust over a range of width of the residual limb. Stable and adjustable medio-lateral support is obtained in directions 42 toward the midline of the socket system by tensioning the straps connecting the anterior and posterior clamp elements.

The anterior clamp element 14 includes an adjustable anatomical section 60 that can be adapted to accept a range of different anatomical shapes of the residual limb. An insert 62, such as a patella tendon bar or pad, may be secured to the anatomical section 60 so as to allow for loading in an anatomically sensitive area. The insert is removable and different inserts having different shapes, sizes, thicknesses, densities and etc. may be used to accommodate different sensitivity levels and geometries of the residual limb.

2. Second Embodiment of the Socket System

Figure 9:
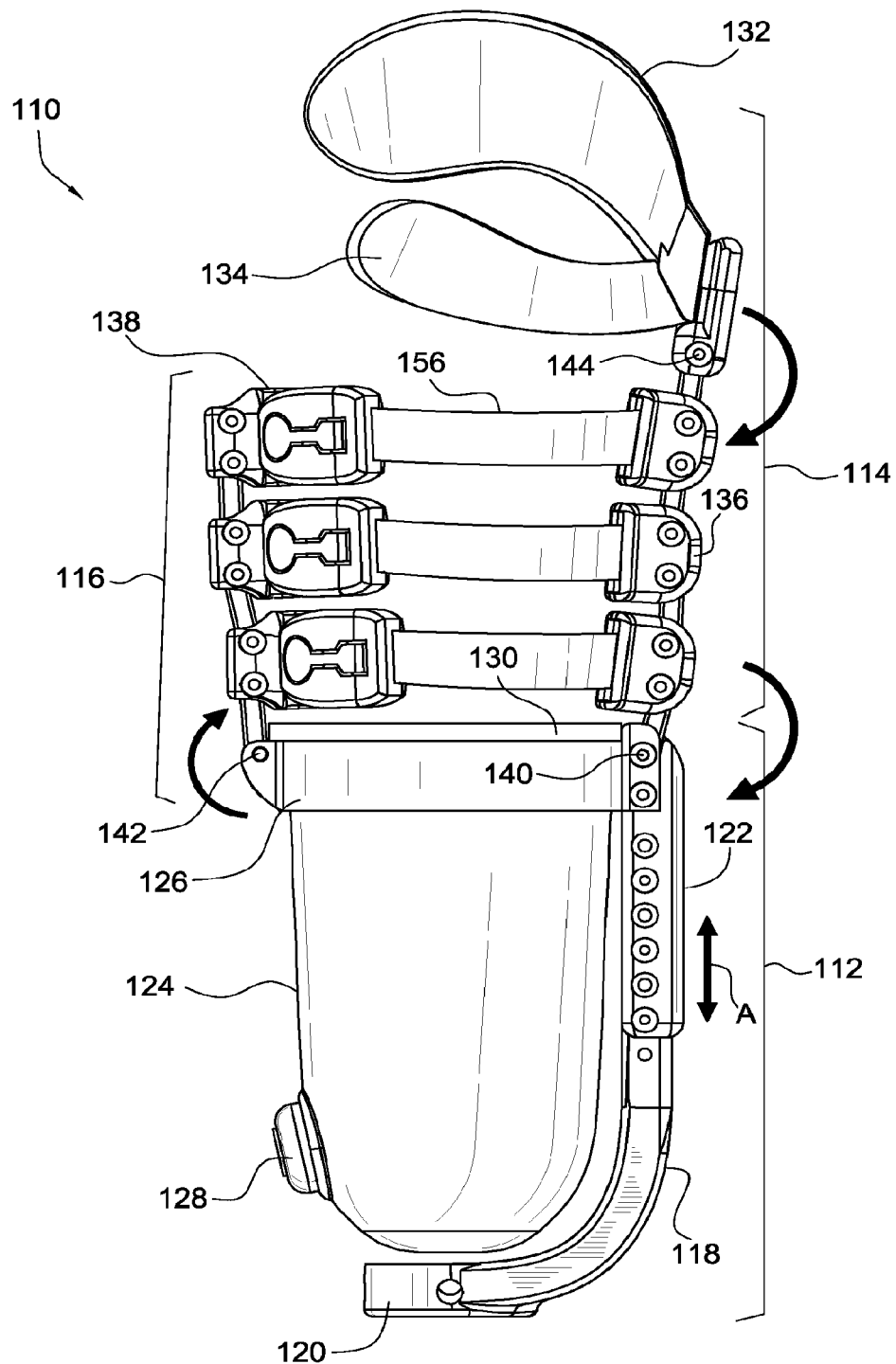
FIG. 9 is an elevational view of another embodiment of a socket system.

FIG. 9 depicts another embodiment of the adjustable socket system 110. According to this embodiment, the socket system 110 includes a distal component 112 adapted to rigidly secure to a residual limb, a proximal anterior component 114 secured to the distal component 112, and a distal posterior component 116 connected to the distal component 112 and the proximal anterior component 114.

The distal component 112 defines a strut base 118 having a base connector 120 defined at a distal end for securing to a prosthetic component system (not shown), such as a foot, pylon and other component. A telescoping strut 122 is slidably and lockingly secured to a proximal end of the strut base 118. The distal component 112 includes a cup 124 adapted to secure to at least a distal portion of the residual limb, and having a valve 128. A ring 126 secures to the telescoping strut 122 and supports the cup 124 with a retaining rim 130 formed by the cup 124.

The proximal anterior component 114 includes an upper wing 132 adapted for securing to a condylar region of a residual limb, and a lower wing 134 adapted for securing to a paratibial region of a residual limb. The proximal anterior component 114 includes a plurality of anterior vertebra 136 arranged for adjustment relative to one another. The proximal posterior component 116 also includes a plurality of posterior vertebra 138 arranged for adjustment relative to one another.

The anterior vertebrae 136 are hingedly connected to the distal component 112 at a hinge 140, and the posterior vertebrae 138 are hingedly connected to the ring 126 at a hinge 142. The upper and lower wings 132, 134 are hingedly connected to the anterior vertebrae 136 at a hinge 144.

Figure 10:
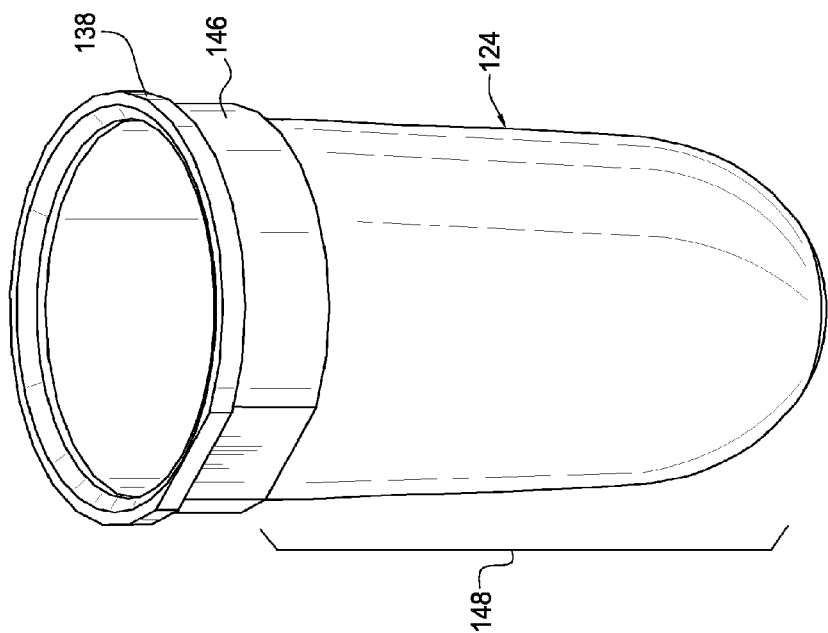
FIG. 10 is a perspective view of a cup of the socket system of FIG. 9.

FIG. 10 illustrates the cup 124 as having a mounting band 146 configured and dimensioned for the ring 126 to secure thereabout. The cup 124 also defines a profile adapted for securing to a general residual limb size.

The cup is preferably preformed and significantly simplifies the design of the socket assembly. It is understood that a third of the residual limb is of a generally known shape and volume, and therefore the cup can accommodate a variety different residual limb sizes. The cup is shaped so as to eliminate or minimize weight bearing at the distal end of the residual limb.

The cup includes the valve 128 so as to be capable of providing suction between the suspension liner and the cup. This allows for better retention of the residual by the socket system.

The cup may be formed from a thin rigid plastic and generally matches the profile of a suspension liner. As is well understood in the art of prosthetic devices, a suspension liner has a matrix or stabilizing umbrella that generally retains a shape of the distal end of the suspension liner. The cup may be pre-formed and provided in a plurality of sizes corresponding to standard suspension liner sizes.

In a variation, the cup can be formed to accommodate residual limb and shape sizes at the distal end of the residual limb. This variation of the cup is obtained by either making the cup semi-rigid, or making the cup flexible with additional supporting elements such as ribs, or providing a strapping arrangement as discussed above.

Figure 11:
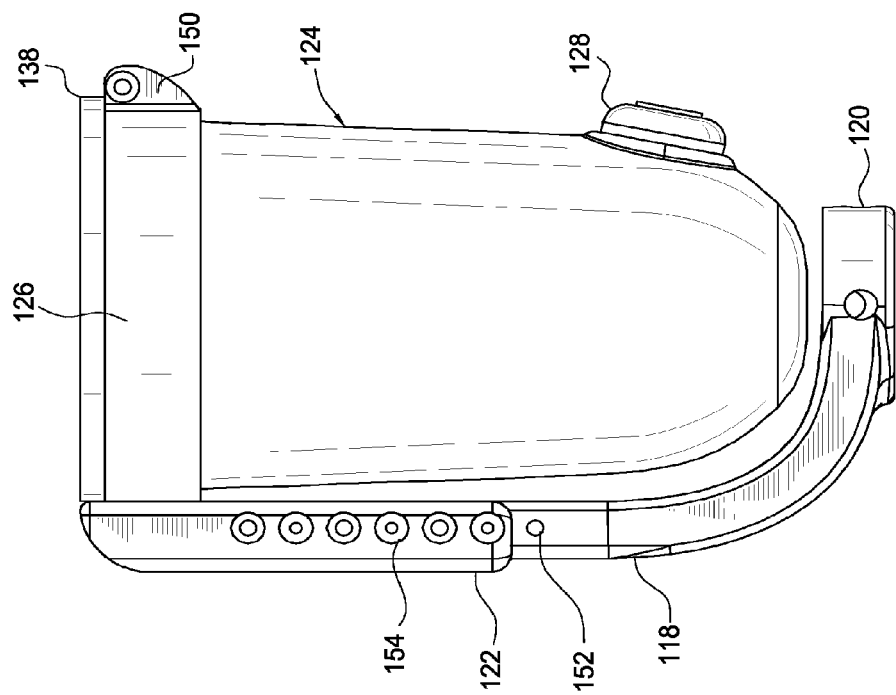
FIG. 11 is an elevational view of a distal component of the socket system of FIG. 9.

FIG. 11 shows the distal component 112 as having the telescoping strut 122 mounted on the strut base 118. The telescoping strut 122 is a sleeve extending over an upper end of the strut base 118, and is selectively mounted at a plurality of height settings of the strut base 118 defined by openings 152 and secured by fasteners 154. The telescoping strut allows for adjustment to the height of the amputee therefore removing the need for a prosthetic pylon.

A bracket 150 is formed on the ring 126 for connection to the proximal posterior component. The ring 126 is preferably formed from a rigid aluminum and is configured and dimensioned to securely fit to the cup 124. In a variation of the ring, the ring may be formed to slightly flex so as to allow for shock absorption yet still provide a weight bearing structure.

FIG. 12 depicts a circumferential vertebrae assembly defined by an anterior vertebra 136, a posterior vertebra 138, and a strap 156 connecting the anterior and posterior vertebra 136, 138. The anterior vertebra 136 defines a link 170, and a cover 158 extending over the link 170 and forming an anterior abutment plate 160 for placement adjacent an anterior aspect of the residual limb. The straps are preferably flexible, which allow for more forgiving retention of a residual limb over known rigid plastic or carbon fiber based sockets.

The posterior vertebra 138 similarly defines a link 186, and a cover 162 extending over the link 186 and forming a posterior abutment plate 164 for placement adjacent a posterior aspect of the residual limb. The abutment plate 164 forms lateral arms 188 upon which a buckle 184 is mounted for receiving the straps 156. The buckle 184 may be a ratcheting type or a clamping type known in the art of buckles for selectively adjusting and maintaining a length of the strap 156. The buckles allow for quick and easy modification of fit for improved comfort.

FIG. 13 shows differently sized circumferences available for securing to differently sized residual limbs, as evidenced by a smaller circumference 166 and a larger circumference 168, each obtained by the circumferential vertebrae assembly.

In reference to FIGS. 14-16, the struts 172 connect the vertebra links 170 to one another. Each of the links 170 is arranged to be fixed in angular position relative to other links by the fasteners 174. As shown, the links can be oriented forward or rearward 176A, 176B relative to one another. The ability to adjust each of the links allows for the socket system to accommodate differently shaped residual limbs, as exemplified in FIG. 16 by the residual limbs 178A, 178B, 178C.

As exemplified by FIG. 15, the struts 172A, 172B can be sized differently relative to one another along the length of the proximal anterior component, or alternatively a clinician can select a single length strut among a plurality of differently sized links for use on the socket system. The arrangement of the differently sized struts permits adjustment in height of the length according to the length of the residual limb.

While the anterior vertebrae assembly is depicted in FIG. 14, a similar construction is likewise obtained by the posterior vertebrae assembly.

Figure 18:
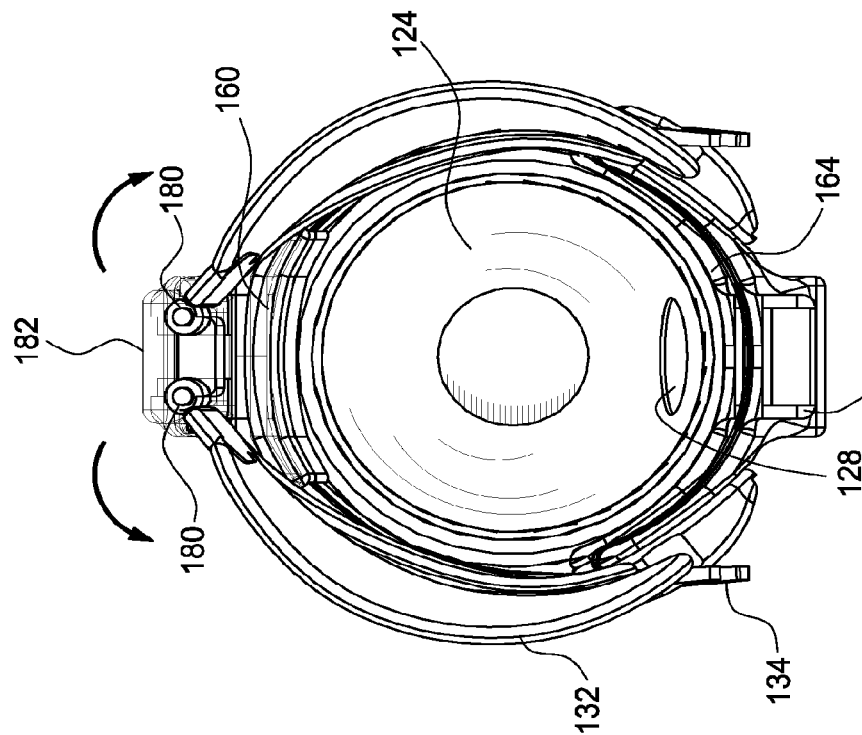
FIG. 18 is a plan view of the socket system of FIG. 9.
Figure 17:
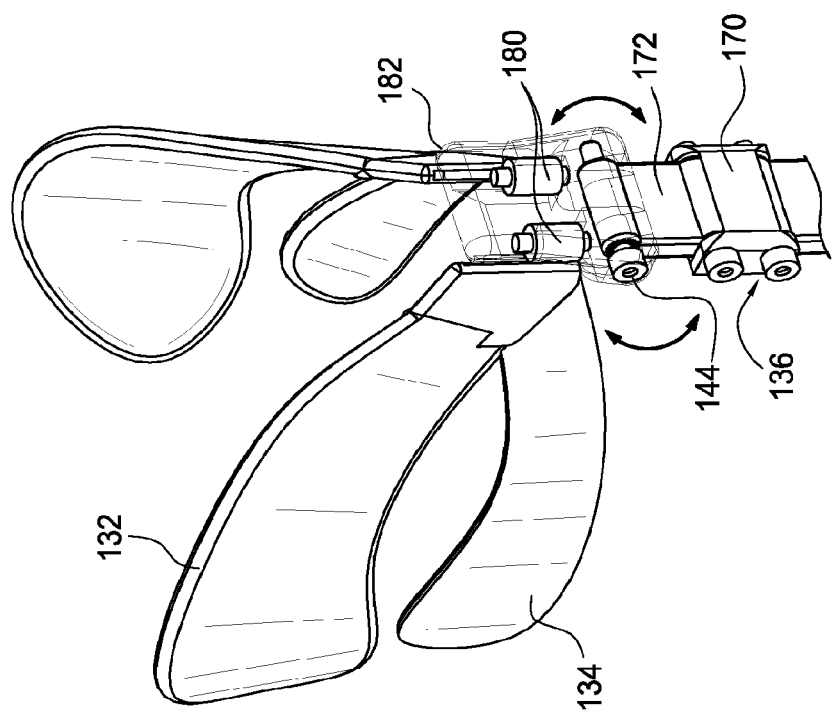
FIG. 17 is a perspective view of condylar wings of the socket system of FIG. 9.

Turning to FIGS. 17 and 18, the upper and lower wings 132, 134 are shown connected to one another, wherein the upper wing 132 is arranged for condylar support of the residual limb whereas the lower wing 134 is arranged for paratibial support. The wings are preferably semi-rigid or at least semi-rigid in certain regions and more flexible in other regions. In a variation of the wings, the wings themselves may secure to straps mounted on the proximal anterior component.

The upper and lower wings 132, 134 are connected at the hinges 180 and hinge 144 to the anterior vertebrae 136. The hinges 180 allow for lateral adjustment of the upper and lower wings 132, 134 relative to the anterior vertebrae 136.

The lateral adjustment of the hinges 180 enables adjustment of the shape and width of the wings by adjusting the distance of the wings relative to the posterior vertebrae 138. A housing 182 is provided over the hinges 180.

3. Third Embodiment of the Socket System

Figure 19:
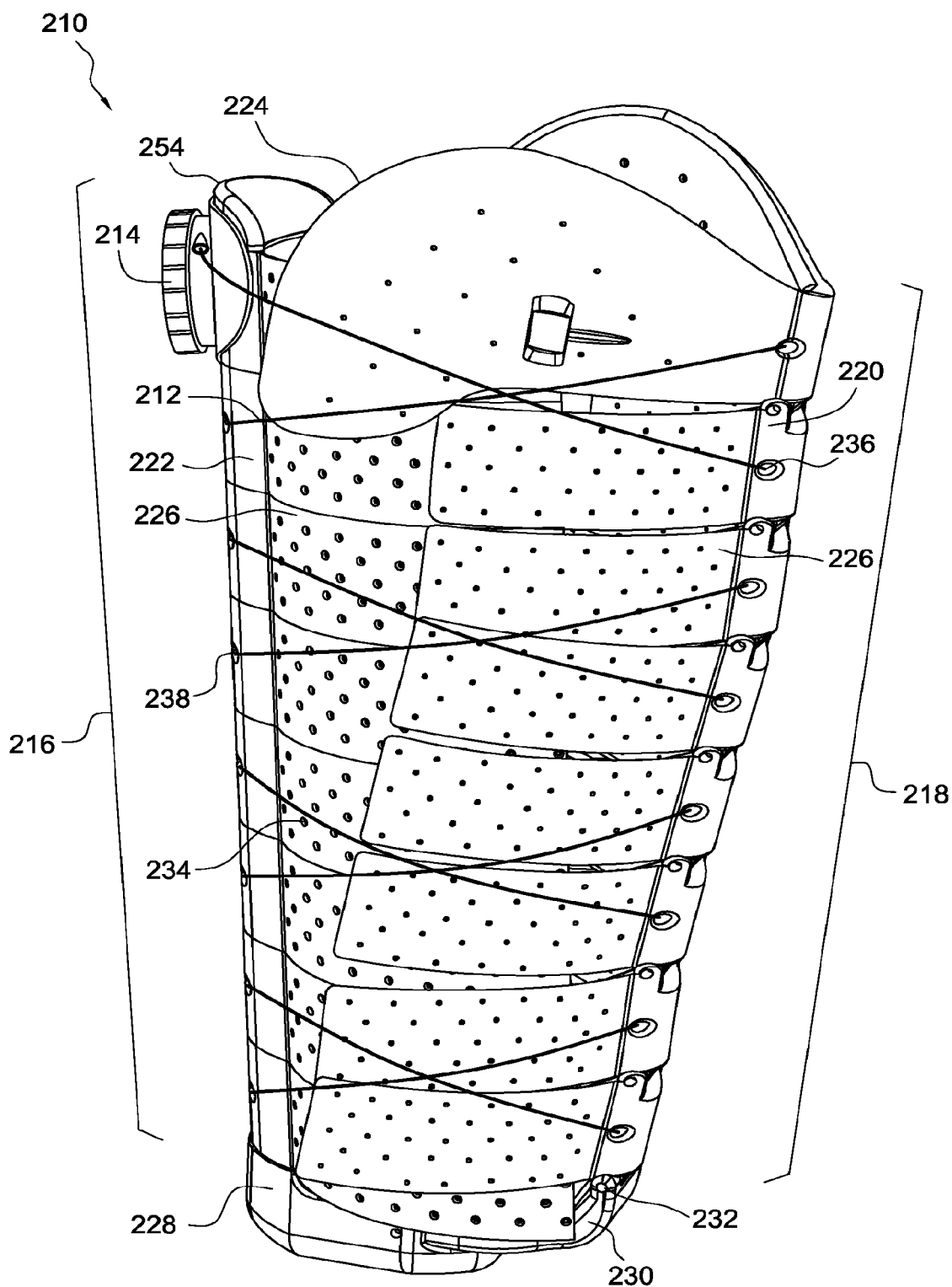
FIG. 19 is a perspective view of an embodiment of the socket system.

FIG. 19 shows another embodiment of the adjustable socket system 210. The socket system 210 includes a rigid spine 216 on the posterior side, a flexible spine 218 on the anterior side, a proximal support 224, lateral flaps 226 extending from either side of the spines 216, 218, and a distal base formed of a posterior distal base component 228 and an anterior distal base component 230. The socket system 210 may be adjusted to the shape and size of the residual limb by adjusting the length of a cable 212 which is threaded around the socket using a dial tensioner 214. The circumference of the socket system 210 may also be adjusted by changing the positions of the distal base components 228, 230. The height of the socket system 210 may further be modified to accommodate the length of residual limb by adding or removing anterior vertebrae 220 and posterior vertebrae 222 to and from the flexible spine 218 and the rigid spine 216, respectively.

The embodiment described with respect to FIG. 19 uses a cable system including a cable 212 as the tensioning element and dial tensioner 214 to adjust the length of the cable 212. The dial tensioner 214 may be turned clockwise to decrease the length of the cable 212 and thereby increase the overall tension of the socket system 210. To decrease the overall tension of the socket system, the dial tensioner 214 may be turned counterclockwise to increase the length of the cable 212. The cable system may be provided by Boa Technology Inc. and is also described in US 2009/0287128.

The cable system provides several advantages in the socket system 210. Since the cable system needs only one tensioner, it is simple for the user to quickly adjust the tension in the entire socket system 210 through the dial tensioner 214. With the dial tensioner 214, the tension on individual areas of the socket system 210 does not have to be adjusted separately. Moreover, because the dial tensioner 214 has rotational increments, the tension in the system may be incrementally increased or decreased to enable the socket system 210 to conform to the specific user's residual limb.

Another advantage of the cable system is that the tension in the socket system 210 may be evenly distributed throughout the socket system 210 which prevents pressure points from forming on different areas of the residual limb. Pressure points on a residual limb are problematic in that the pressure points cause irritation, pain, and discomfort to the residual limb.

The cable system and the flexible spine 218 enable the user to adjust the socket system 210 to suit the user's individual needs and specific residual limb shape. In summary, the cable system on the adjustable socket system 210 provides the user with a simple and fast way to adjust the socket system 210 while increasing the comfort and improving conformability of the socket system compared to conventional sockets.

While the embodiment described with respect to FIG. 19 uses a cable system including a cable 212 as the tensioning element and a dial tensioner 214 to adjust the length of the cable 212, the socket system 210 may be adapted to be used with a variety of tensioning elements including the strap systems of the previous embodiments, wires, laces, and commercially available buckle and strap type systems as would be understood by the skilled person. Further, the socket system 210 may be adapted for use with or without a prosthetic liner.

Figure 20:
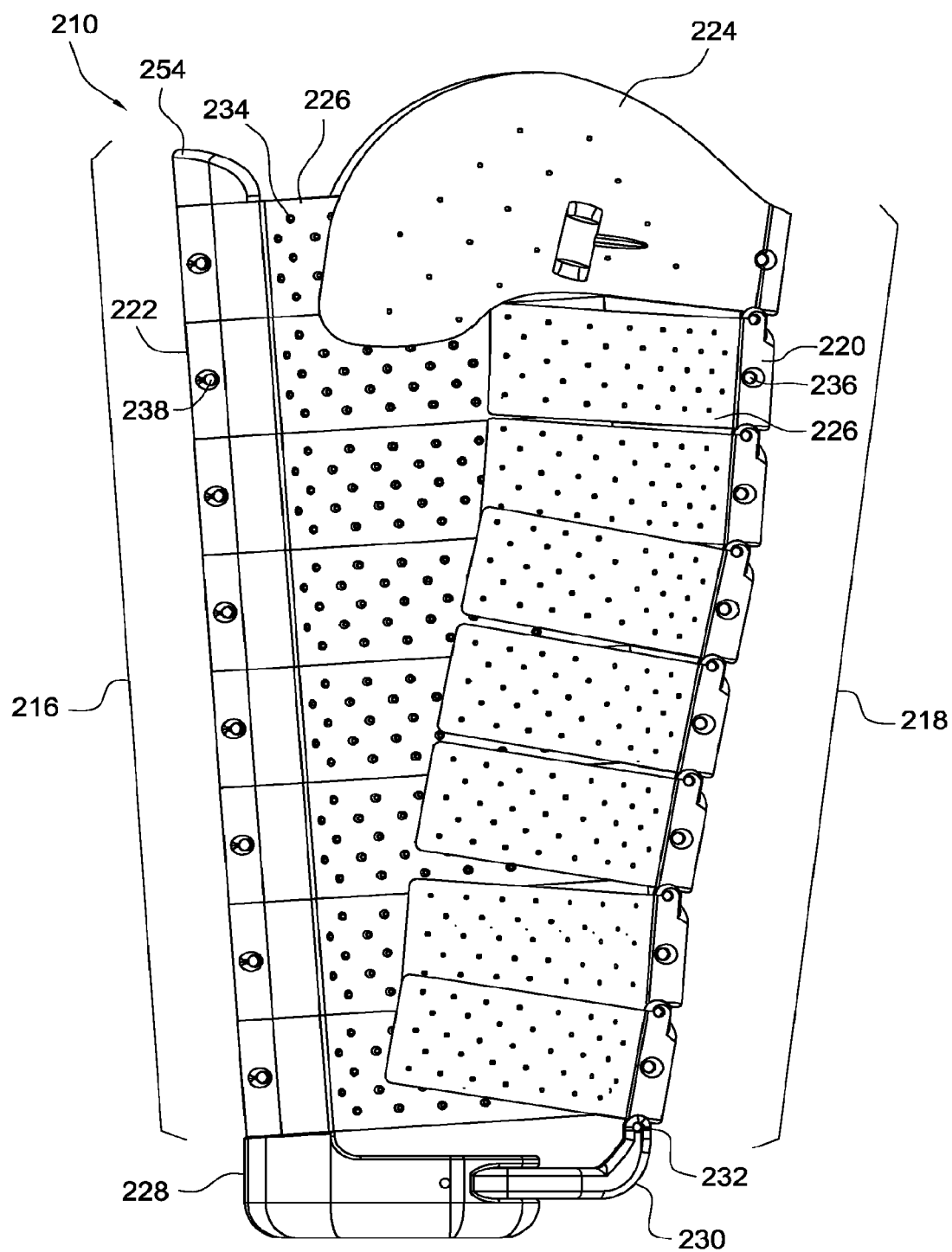
FIG. 20 is a side view of the socket system of FIG. 19.

FIG. 20 is a side view of the socket system 210 without the cable system shown in FIG. 19. The rigid spine 216 includes a plurality of posterior vertebrae 222, a proximal end, and a distal end. The proximal end includes a proximal end component 254, and the distal end is attached to the posterior distal base component 228. The rigid spine 216 is arranged to be angled relative to the longitudinal axis of the socket system 210, preferably having an angle between 0° to approximately 8° from the longitudinal axis.

The flexible spine 218 includes a plurality of anterior vertebrae 220, a proximal end, and a distal end. The proximal end includes a proximal support 224 while the distal end is hingedly attached to the anterior distal base component 230.

The anterior vertebrae 220 and posterior vertebrae 222 are arranged to have an equal number of vertebrae in each of the spines 216, 218 such that the anterior vertebrae 220 have a corresponding posterior vertebra 222. Alternatively, the spines 216, 218 may have an unequal number of vertebrae.

As shown in FIGS. 19 and 20, each of the anterior vertebrae 220 and posterior vertebrae 222 has flaps 226 extending laterally on each side of the vertebrae 220, 222. The lateral flaps 226 have a length such that when the socket system 210 is worn on the residual limb, the anterior flaps at least partially overlap the corresponding posterior flaps.

Figure 21:
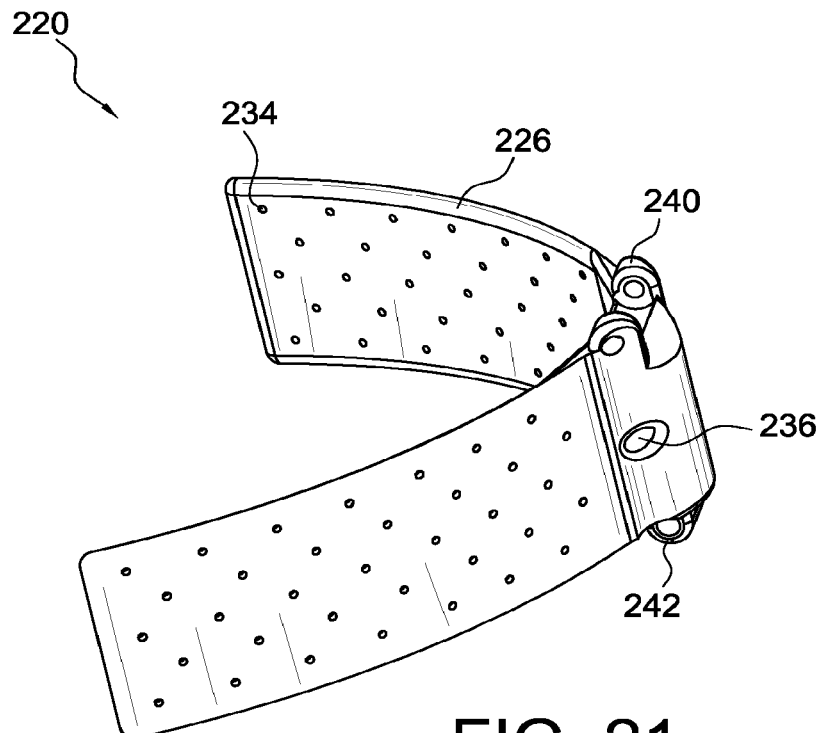
FIG. 21 is a perspective view of an anterior vertebra of the socket system of FIG. 19.

In reference to FIG. 21, a single anterior vertebra 220 is shown. The anterior vertebra 220 in combination with the lateral flaps 226 has overall a circular shape which allows the anterior side of the socket system 210 to conform around the residual limb. The proximal hinge connector 240 of the anterior vertebra 220 is connected to the distal hinge connector 242 of a second anterior vertebra 220 with a hinge pin. The hinge pin is configured to enable the proximal hinge connector 240 and the distal hinge connector 242 to pivot about the hinge pin. Using a plurality of hingedly connected anterior vertebrae 220, a flexible spine 218 is formed which conforms to the specific shape of the residual limb. While the hinge shown in this embodiment uses a hinge pin, a variety of different types of hinge joints may be used as would be understood by the skilled person.

Figure 22:
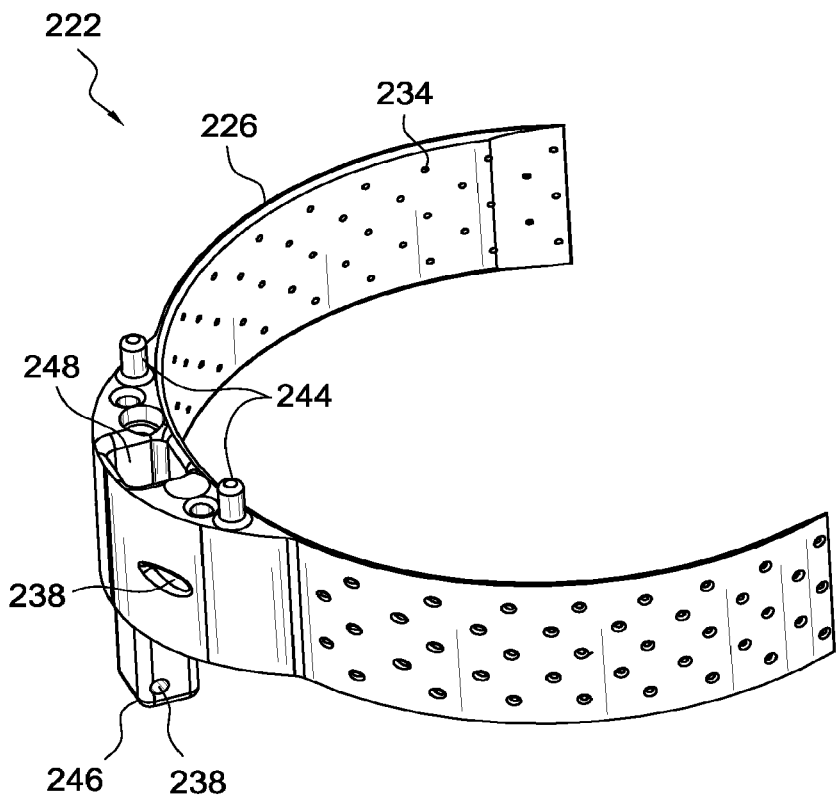
FIG. 22 is a perspective view of a posterior vertebra of the socket system of FIG. 19.

FIG. 22 illustrates a single posterior vertebra 222. A plurality of posterior vertebrae 222 forms the rigid spine 216. Each posterior vertebra 222 includes a pair of proximal posts 244 that engages corresponding distal recesses of a second posterior vertebra 222 located on either side of the distal post 246. On the distal side of the posterior vertebra 222, the hollow distal post 246 protrudes towards the distal end of the rigid spine 216. The distal post 246 fits within a longitudinal opening 248 of another posterior vertebra 222. The distal post 246 further includes an opening at the distal end to allow cables or cables to pass longitudinally through the rigid spine 216. Since the distal post 246 extends past the opening 238, the sides of the distal post 246 are provided with corresponding openings 238 to allow the cable 212 to pass through the posterior vertebra 222.

The lateral flaps 226 which extend from each side of the anterior and posterior vertebra 220, 222 are discussed with reference to FIGS. 19-22. The lateral flaps 226 may be formed with the vertebrae 220, 222 together as a single component. Alternatively, the lateral flaps 226 may be detachable from the vertebrae 220, 222 and may be attached to the vertebrae 220 in a variety of ways including mechanical attachments or adhesives as would be understood by a skilled person. As shown in FIGS. 21 and 22, the lateral flap 226 forms a continuous, smooth inner surface with the vertebra with which the lateral flap 226 is attached.

The lateral flaps 226 may be formed from a semi-rigid material such as plastic. It is highly desirable that the lateral flaps 226 be breathable to increase the comfort of the residual limb within the socket system 210. In view of this desire, the lateral flaps 226 are provided with perforations 234 to allow circulation of air through the flaps and around the residual limb.

The lateral flaps 226 may further be lined on the interior side with different materials such as a textile material, polymeric material, medical grade foam or a combination thereof. Different types of lining material may also be used on different flaps 226 to target the specific area of the residual limb with which the flaps 226 will come into contact. For example, the medical grade foam may be applied to a flap 226 which supports the fibula head of a residual limb for added cushioning.

Figure 23:
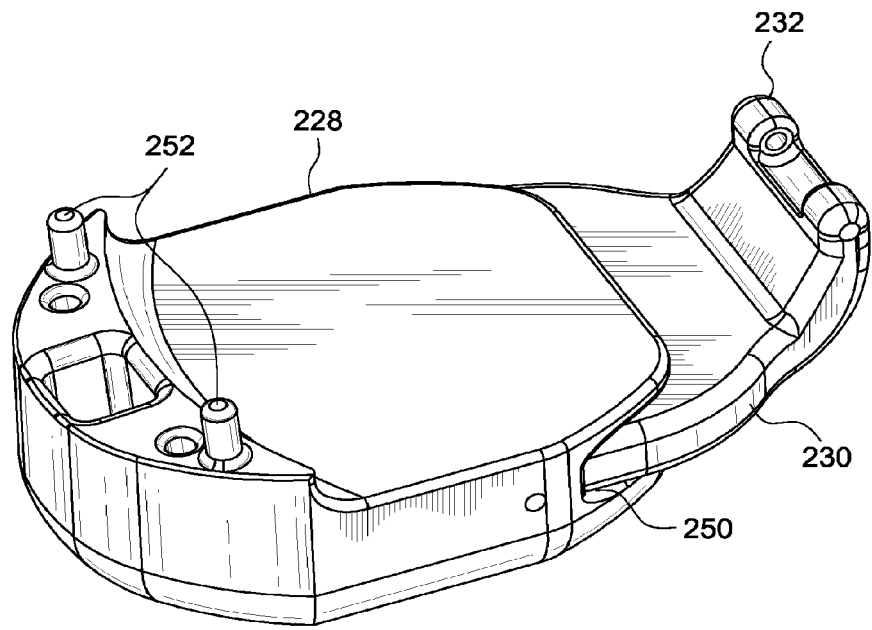
FIG. 23 is a perspective view of the distal base of the socket system of FIG. 19.

FIG. 23 shows the distal base of the socket system 210 having two components 228, 230. The posterior base component 228 has a recess 250 configured to receive the anterior base component 230. The anterior base component 230 slidably engages the posterior base component 228. The anterior base component 230 may be locked into different positions with respect to the posterior base component 228 resulting in different circumferences for the socket system 210.

The posterior base component 228 and the anterior base component 230 have raised anterior and posterior sides as can be seen in FIG. 23 and substantially form a cup to receive the distal end of a residual limb. Since the posterior end of the rigid spine 216 is connected to the posterior base component 228, the posterior base component 228 likewise has a pair of base posts 252 and a recess similar to the proximal posts 244 and recess 250 of the posterior vertebra 222.

The anterior base component 230 hingedly connects to the distal end of the flexible spine 218 similar to how each anterior vertebra 220 is connected to each other. The anterior base component 230 has a base spine connector 232 similar to the proximal hinge connector 240 of the anterior vertebra 220.

The posterior base component 228 is adapted to be attached to a prosthetic limb such as the pylon of a prosthetic limb or a prosthetic foot and is made from a substantially rigid material to support the weight placed on the prosthetic limb. The posterior base component 228 and the anterior base component 230 may be made of plastic, for example ABS plastic.

Figure 24:
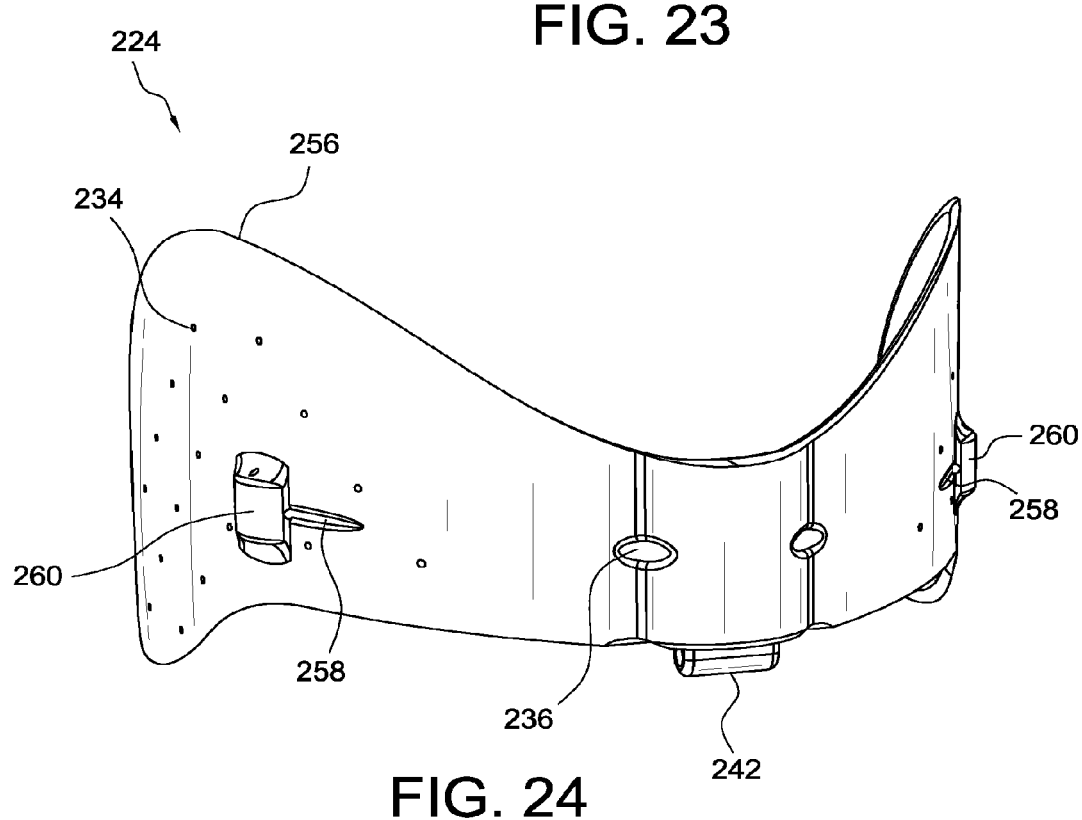
FIG. 24 is a perspective view of the proximal support of the socket system of FIG. 19.

FIG. 24 depicts a proximal support 224 which is attached on the proximal end of the flexible spine 218. The proximal support 224 has a pair of wings 256 extending on either side of the vertebra component of the proximal support 224. The wings 256 are arranged for condylar support of the residual limb. Similar to the anterior vertebra 220, the proximal support 224 has openings 236 through which the cable 212 is able to pass and a distal hinge connector 242. The wings 256 may have a second opening 258 for the cable 212 which is formed from a groove in the wings 256 and a raised surface 260 under which the cable 212 passes. The wings 256 are also provided with perforations 234 similar to the lateral flaps 226. In addition to the perforations 234, the wings may be lined with materials similar to those used in lining the lateral flaps 226 for added comfort and support.

While the embodiments have been described herein with respect to specific tensioning elements, a variety of tensioning elements may be used with the socket system including cables, wires, straps, laces or any other device used to provide and maintain tension as would be understood by the skilled person.

4. Closing

From the features of the adjustable socket system described above, an adjustable socket system is provided that provides simple and quick adjustment to the volume and shape of the socket system, and hence to a residual limb supported by the socket system. In short, the socket system departs from the conventional static socket type and instead allows for adjustment in height, volume and shape, thus permitting adjustment to assure stable fitting of the socket. Further, the socket system accommodates a variety of differently sized residual limbs, and is not constrained to a particular amputee but can be used by a variety of amputees.

While the foregoing embodiments have been described and shown, it is understood that alternatives and modifications of these embodiments, such as those suggested by others, may be made to fall within the scope of the invention. Any of the principles described herein may be extended to other types of prosthetic or orthopedic devices.

The invention claimed is:

1. An adjustable prosthetic socket having proximal and distal ends and an axis extending between the proximal and distal ends, comprising:
    a distal base adapted to support a distal portion of a residual limb and located at the distal end of the socket, the distal base including:
        a first base component defining a recess inside a lower part of the first base component; and
        a second base component including a horizontally projecting part slidably received within the recess, wherein the recess defines a side opening and walls extending over and under the horizontally projecting part of the second base component, wherein the first base component defines a first raised side and the second base component defines a second raised side forming a cup shaped to fit the distal portion of the residual limb;
    first and second spines extending upwardly from the distal base toward the proximal end and defining at least part of a circumference of the socket about the axis, the first spine being attached to the first base component and the second spine being attached to the second base component, wherein the second spine pivots toward and away from the first spine about a hinge connection between the second spine and the second base component, wherein the second base component is lockable at a plurality of different radial positions within the recess to selectively adjust the circumference of the socket;
    a proximal support attached to the second spine and extending from the second spine, the proximal support arranged to distribute pressure from the second spine over a portion of the residual limb; and
    a tensioning system operatively connected to the spines and arranged to selectively adjust the circumference of the socket.

2. The socket of claim 1, wherein the tensioning system includes:
    at least one tensioning element operatively connected to the spines; and
    at least one tensioning mechanism attached to the at least one tensioning element and arranged to selectively tension the at least one tensioning element to adjust the circumference of the socket.

3. The socket of claim 2, wherein the at least one tensioning element comprises a strap, and the at least one tensioning mechanism comprises a strap tensioner.

4. The socket of claim 2, wherein the at least one tensioning mechanism comprises a ratcheting system.

5. The socket of claim 2, wherein the at least one tensioning element is secured at or near the proximal end of the socket.

6. The socket of claim 1, wherein the proximal support defines an inner surface arranged to contact and support a part of the residual limb.

7. The socket of claim 1, wherein the proximal support extends circumferentially beyond at least one side of the second spine.

8. The socket of claim 1, wherein the proximal support includes one or more wings.

9. The socket of claim 1, wherein an interior surface of the second spine defines a shape arranged to substantially correspond to a shape of the residual limb.

10. An adjustable prosthetic socket having proximal and distal ends and an axis extending between the proximal and distal ends, comprising:
    a distal base adapted to support a distal portion of a residual limb and located at the distal end of the socket, the distal base including a first base component defining a recess inside a lower part of the first base component, and a second base component including a horizontally projecting part slidably received within the recess, wherein the first base component defines a first raised side and the second base component defines a second raised side forming a cup shaped to fit the distal portion of the residual limb;
    first and second spines extending upwardly from the distal base toward the proximal end and defining at least part of a circumference of the socket about the axis, the first spine attached to the first base component and the second spine attached to the second base component, wherein the second base component is lockable at a plurality of different radial positions within the recess to selectively adjust the circumference of the socket;
    a plurality of lateral flaps extending from sides of the first and second spines, the lateral flaps defining at least part of the circumference of the socket about the axis and having a dimension which allows for some overlap between anterior ones of the lateral flaps and posterior ones of the lateral flaps when the socket is worn on the residual limb; and
    a tensioning system operatively connected to the first and second spines and arranged to selectively adjust the circumference of the socket.

11. The socket of claim 10, wherein an interior side of the lateral flaps includes a cushioning material.

12. The socket of claim 10, wherein the lateral flaps are formed separate from the first and second spines.

13. An adjustable prosthetic socket having proximal and distal ends and an axis extending between the proximal and distal ends, comprising:
    a distal base adapted to support a distal portion of a residual limb and located at the distal end of the socket, the distal base including a first base component defining a recess inside a lower part of the first base component, and a second base component including a horizontally projecting part slidably received within the recess, wherein the first base component defines a first raised side and the second base component defines a second raised side forming a cup shaped to fit the distal portion of the residual limb;

first and second spines extending upwardly from the distal base toward the proximal end and defining at least part of a circumference of the socket about the axis, the first spine being attached to the first base component and the second spine being attached to the second base component, wherein the second spine pivots toward and away from the first spine about a hinge connection between the second spine and the second base component, wherein the second base component is lockable at a plurality of different radial positions within the recess to selectively adjust the circumference of the socket;

a proximal support attached to the second spine and extending from the second spine, the proximal support arranged to distribute pressure from the second spine over a portion of the residual limb; and a tensioning system operatively connected to the spines and arranged to selectively adjust the circumference of the socket.

14. The socket of claim 13, wherein the proximal support defines an inner surface arranged to contact and support a part of the residual limb.

\* \* \* \* \*